(12) United States Patent
Menzel et al.

(10) Patent No.: US 10,669,435 B2
(45) Date of Patent: Jun. 2, 2020

(54) PROCESS FOR PRODUCING AN ANTIBACTERIAL COATING COMPOSITION FOR IMPLANTS

(71) Applicant: Gebr. Brasseler GmbH & Co. KG, Lemgo (DE)

(72) Inventors: Henning Menzel, Lehrte (DE); Marco Wassmann, Mengershausen (DE); Sebastian Stelljes, Hannover (DE); Meike Stiesch, Hannover (DE); Andreas Winkel, Hannover (DE)

(73) Assignee: GEBR. BRASSELER GMBH & CO. KG, Lemgo (DE)

( * ) Notice: Subject to any disclaimer, the term of this patent is extended or adjusted under 35 U.S.C. 154(b) by 470 days.

(21) Appl. No.: 15/278,874

(22) Filed: Sep. 28, 2016

(65) Prior Publication Data

US 2017/0096565 A1 Apr. 6, 2017

(30) Foreign Application Priority Data

Oct. 2, 2015 (DE) .................. 10 2015 219 139

(51) Int. Cl.
*C09D 5/14* (2006.01)
*A61L 27/54* (2006.01)
(Continued)

(52) U.S. Cl.
CPC ............... *C09D 5/14* (2013.01); *A61F 2/02* (2013.01); *A61L 27/54* (2013.01); *C09D 151/08* (2013.01);
(Continued)

(58) Field of Classification Search
CPC . C09D 5/14; C09D 151/08; A61F 2/02; A61F 2310/0097; A61F 2300/404
See application file for complete search history.

(56) References Cited

U.S. PATENT DOCUMENTS

| 5,925,552 A | 7/1999 | Keogh et al. |
| 2006/0045899 A1* | 3/2006 | Sarangapani ......... A01N 25/10 424/405 |
| 2006/0140883 A1* | 6/2006 | Trivedi ................ A61K 8/21 424/58 |

FOREIGN PATENT DOCUMENTS

| CN | 104592459 A | * | 5/2015 |
| RU | 2264337 C1 | | 11/2005 |

OTHER PUBLICATIONS

Waßmann, Marco "Bonding of copolymers and Active Substances to produce Antibacterial Coating on Dental Implants" Dissertation Mar. 28 2015, ISBN 978-3-8439-2324-8 Selected pages with partial translation (Year: 2015).*

(Continued)

*Primary Examiner* — Ling Siu Choi
*Assistant Examiner* — David L Miller
(74) *Attorney, Agent, or Firm* — Shuttleworth & Ingersoll, PLC; Timothy J. Klima

(57) ABSTRACT

A process for producing an antibacterial coating composition for implants. The process includes the steps i) reaction of a monomer A which is based on (meth)acrylic acid and contains at least one epoxide with a polyguanidine by reaction of an amino group of the polyguanidine with the epoxide to give a (meth)acrylic acid-polyguanidine macromolecule and ii) polymerization of the (meth)acrylic acid-polyguanidine macromolecule with a monomer B which contains at least one polymerizable double bond and at least one phosphonate group by free-radical polymerization of the (meth)acrylic acid unit and the double bond.

14 Claims, 4 Drawing Sheets

Figure 1:
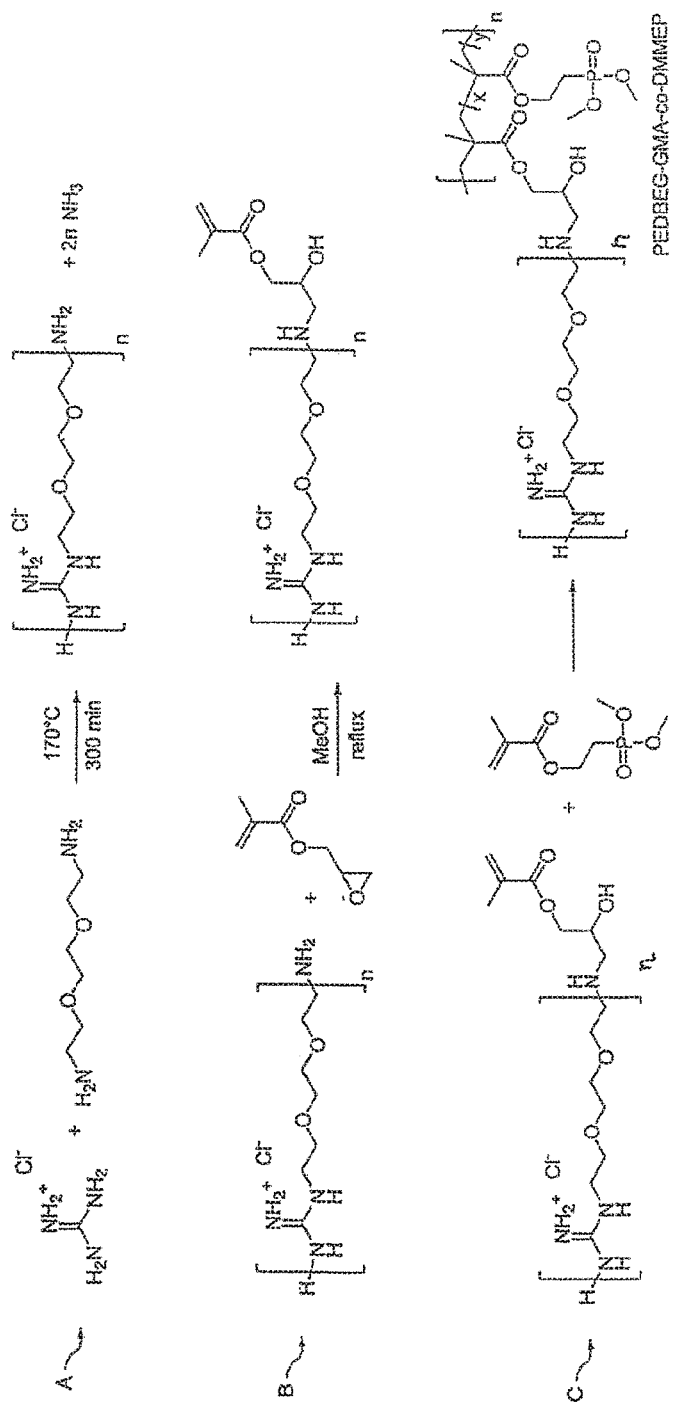

(51) Int. Cl.
*A61F 2/02* (2006.01)
*C09D 151/08* (2006.01)
(52) U.S. Cl.
CPC ................. *A61F 2310/0097* (2013.01); *A61F 2310/00401* (2013.01); *A61F 2310/00407* (2013.01); *A61F 2310/00485* (2013.01); *A61F 2310/00544* (2013.01); *A61L 2300/404* (2013.01)

(56) References Cited

OTHER PUBLICATIONS

German Office Action dated Apr. 12, 2017 from counterpart German App No. 10 2015 219 139.7.
Order of the Faculty of Life Sciences Technical University of Braunschweig, Dec. 22, 2011.
European Search Report dated Mar. 13, 2017 for counterpart European Application No. 16188141.2.

\* cited by examiner

PROCESS FOR PRODUCING AN ANTIBACTERIAL COATING COMPOSITION FOR IMPLANTS

This application claims priority to German Patent Application No. 102015219139.7 filed Oct. 2, 2015, the entirety of which is incorporated by reference herein.

The invention relates to a process for producing an antibacterial coating composition for implants which has very good cell compatibility and excellent antibacterial action. In addition, the present invention also relates to an antibacterial implant coating composition and a process for coating an implant and an antibacterially coated implant.

Implants are used in many medical disciplines for the reconstruction of organ and tissue functions. They consist of artificial materials to which bacteria can adhere and on which these can become organized into complex biofilm colonies. The inflammation reactions resulting therefrom and associated progressive destructive processes in the tissue lead to a loss of function of the implant and considerable adverse effects on the patient. In dentistry in particular, periimplantational infections having a prevalence of 30% are of great clinical importance. Owing to the high resistance of bacterial biofilms to chemical therapeutic agents, removal of biofilms in dentistry is effected predominantly mechanically, with many regions of the dental implant being able to be reached only incompletely because of the complex geometry.

The problem of implant-associated infections is at present combated by coating the implant with silver. The silver layer prevents adhesion of bacteria, but also the adhesion of cells belonging to the body, i.e. it is not selective. A new development comprises antibacterial polymers which are applied to the implant materials. However, polymers developed up to now either do not have a sufficient cell compatibility or do not have a satisfactory antibacterial action. A further problem is reliable and technically implementable application of the polymers to the surface.

Proceeding from this prior art, it is an object of the invention to provide a process for producing an antibacterial coating composition for implants, which can be implemented simply without great technical complication and makes it possible to produce a coating composition having a high cell compatibility combined with a very good antibacterial function. In addition, it is an object of the present invention to provide an antibacterial implant coating composition which is simple to apply, adheres well to the implant and has very good cell compatibility combined with good antibacterial action. A further object of the present invention is to provide a process for coating an implant with an antibacterial coating, which produces a uniformly covering coating adhering to the implant and avoids a high degree of technical complication. Furthermore, it is an object of the present invention to provide an antibacterially coated implant which displays high cell compatibility combined with a very good antibacterial function.

These objects are achieved by features disclosed herein.

Accordingly, the object is achieved by a process for producing an antibacterial coating composition for implants, which comprises the following steps: i) reaction of a monomer A which is based on (meth)acrylic acid and contains at least one epoxide with a polyguanidine by reaction of an amino group of the polyguanidine with the epoxide to give a (meth)acrylic acid-polyguanidine macromolecule and ii) polymerization of the (meth)acrylic acid-polyguanidine macromolecule with a monomer B which contains at least one polymerizable double bond and at least one phosphonate group by free-radical polymerization of the (meth)acrylic acid unit and the double bond.

For the purposes of the invention, the term "compounds which are based on (meth)acrylic acid", for example "monomer A which is based on (meth)acrylic acid", "(meth)acrylic acid-polyguanidine macromolecule", "(meth)acrylic acid unit", "(meth)acrylic acid group" and the like, refers to a compound based on propenoic acid, i.e. acrylic acid, or a compound based on 2-methylpropenoic acid, i.e. methacrylic acid, namely, according to the abovementioned examples: "monomer A which is based on methacrylic acid", "methacrylic acid-polyguanidine macromolecule", "methacrylic acid unit", "methacrylic acid group". In the interest of simplicity, the abbreviation "(meth)acrylic acid . . . " will be used in the following description to represent "acrylic acid . . . " and "methacrylic acid . . . ".

For the purposes of the present invention, polyguanidines are derivatives of oligoguanidines which can be synthesized by reaction of diamines with guanidine hydrochloride. Polyguanidines are known for combating microorganisms and are often used in disinfectants, detergents and cleaners or cosmetics. Owing to their high solubility in water, they are, in the form employed up to now, unsuitable for coating implants. Reaction of the polyguanidine with the monomer A which contains at least one epoxide and is based on (meth)acrylic acid gives a polymerizable macromolecule, viz. a (meth)acrylic acid-polyguanidine macromolecule, the (meth)acrylic acid unit of which introduces a potential polymerization function. It thus becomes possible to join a further monomer to the (meth)acrylic acid-polyguanidine macromolecule by polymerization and thus reduce the solubility in water by formation of a polymeric film. The monomer B provided for this purpose according to the invention has a high compatibility with the (meth)acrylic acid-polyguanidine macromolecule. The phosphonate group gives the resulting polymer an anchor function for binding to conventional implant materials such as titanium, stainless steel, zirconium, tantalum, zirconium oxide and the like. The coating composition of the invention is thus self-binding. It requires no additional adhesive component. This assists application of the coating composition to the implant and allows coatings on even geometrically complex implant surfaces. Due to the (meth)acrylic acid-based basic structure of the monomer A, the double bond function of the monomer B and the polyguanidine, the coating composition produced has a high microbial selectivity. This means that the cell compatibility is high while at the same time the antibacterial action is very good. Alternative processes which firstly provide for bonding of an anchor function to an implant surface and subsequent reaction with an antibacterially active substance have, in contrast, led to no satisfactory effect in respect of reducing germs. The coating composition produced according to the invention also makes good adhesion of human tissues to the implant surface possible, which is a main prerequisite for avoidance of destructive processes. The process can be implemented simply without great technical complication and allows coating of metallic and ceramic implants which interact with phosphonate-containing groups, even those having complex geometries, which firstly significantly reduces or avoids colonization of the implant by pathogenic germs and secondly does not prevent the adhesion of cells belonging to the body. Thus, implant-associated infections can be effectively avoided.

The present disclosure contains advantageous further developments and embodiments.

In an advantageous further development of the process of the invention, the monomer A is 2,3-epoxypropyl methacrylate (glycidyl methacrylate—GMA). This monomer has been found to be particularly biocompatible with human tissue and is very readily processable in the process of the invention. 2,3-Epoxypropyl methacrylate is sterically unhindered and can thus react with the polyguanidine at a high reaction rate.

Furthermore, the monomer B is advantageously diethyl (4-vinylbenzyl)phosphonate (VBP), 2-(dimethoxyphosphoryl)ethyl methacrylate (DMMEP) or 2-(dimethoxyphosphoryl)methyl methacrylate (DMMMP). These monomers allow very rapid and complete polymerization with the double bond of the (meth)acrylic acid group in the monomer A. They have good cell compatibility and offer a secure anchoring function to conventional implant surfaces.

It is also advantageous to use poly-2-(2-ethoxy)ethoxyethylguanidine hydrochloride (CAS Registry Number 374572-91-5) (PEDBEG) as polyguanidine. This polyguanidine has good cell compatibility combined with a very good antibacterial action.

A further advantageous embodiment of the process provides for the PEDBEG to be prepared by reaction of guanidine hydrochloride with 1,2-bis(2-aminoethoxy)ethane and to have at least one of the following formulae:

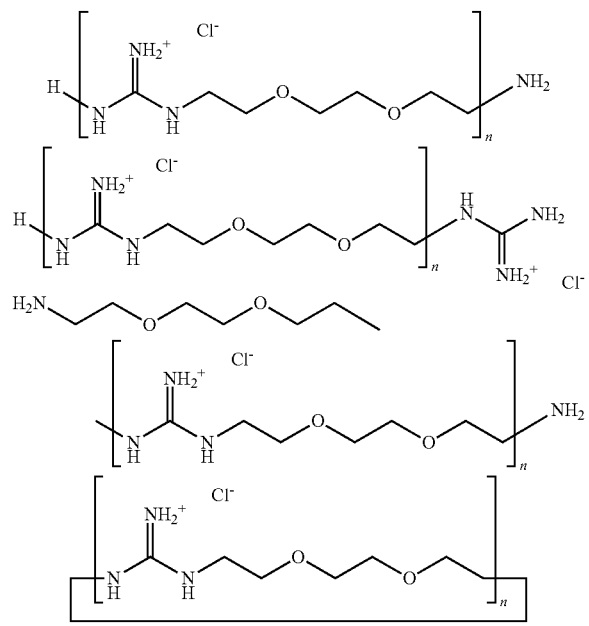

where n is an integer in the range from 1 to 10, preferably from 3 to 6, and is in particular 5. This polyguanidine displays a particularly good antibacterial action combined with a very good cell compatibility.

The reaction for producing the coating composition can be assisted by the polyguanidine having a molecular weight of from 800 to 1300 g/mol.

The adhesion of the coating composition to be produced to an implant can be improved at a not significantly reduced antibacterial action by the proportion of the monomer B based on the antibacterial coating composition being about 67 mol %.

An antibacterial implant coating composition is likewise described according to the invention. The implant coating composition is produced by the above-described process, with the indicated advantageous further developments of the process of the invention also being applicable to the implant coating composition of the invention. As disclosed above, according to the invention the polyguanidine is firstly reacted with the monomer A to form a macromonomer and only then is a copolymerization with the monomer B carried out, instead of monomers A and B firstly being copolymerized and the copolymer only then being reacted with the polyguanidine. Although similar product structures can theoretically be postulated for the two reaction routes, only the process according to the invention leads to an implant coating composition having a high antibacterial activity. This has been confirmed by inoculation tests. It is therefore assumed that the chemical structure of the implant coating composition of the invention differs from the structure obtained using the same starting materials but by reaction in a different order. The implant coating composition produced according to the invention displays very good adhesion to conventional implant surfaces combined with high cell compatibility and good antimicrobial activity.

The invention also describes a process for coating an implant with an antibacterial coating. The process comprises production of a coating composition, which comprises the steps i) reaction of a monomer A which is based on (meth)acrylic acid and contains at least one epoxide with a polyguanidine by reaction of an amino group of the polyguanidine with the epoxide to give a (meth)acrylic acid-polyguanidine macromolecule and ii) polymerization of the (meth)acrylic acid-polyguanidine macromolecule with a monomer B which contains at least one polymerizable double bond and at least one phosphonate group by free-radical polymerization of the (meth)acrylic acid unit and the double bond to produce a coating composition. The process steps presented here correspond to the process steps of the process of the invention for producing an antibacterial coating composition. Reference is therefore made to the above disclosure of the process of the invention. The coating composition obtained in this way is dissolved in a solvent in step iii). The solvent is not subject to any particular restrictions and is selected according to the solubility of the coating composition. Alcohols such as methanol, ethanol and isopropanol have been found to be advantageous. A solution of the coating composition, which can also be colloidal, is obtained. In a further process step iv), an implant is provided and is degreased. Degreasing can, for example, be effected by cleaning with solvents such as acetone, dichloromethane, methanol and the like or by means of plasma cleaning. After optional drying, the solution of the coating composition is subsequently applied to the implant in step v). As a result of the coating composition being present in the form of a solution, many simple, conventional application processes can be employed, which keeps the technical complication of the process small. Application to geometrically complex surfaces is also simplified in this way. Binding of the coating composition to the implant is finally carried out in step vi). This is effected by the action of temperatures in the range from 50 to 200° C., for example in a drying oven or another suitable oven. As a result of the binding step, the polymeric coating composition becomes attached to the surface of the implant and binds covalently to the implant via the phosphonate groups. The binding force of the bond between the implant surface and the coating composition is high. Application of an adhesive can thus be dispensed with. The process gives, without great technical complication, an implant having a durably high antimicrobial activity combined with very good cell compatibility.

The advantages, advantageous further developments and embodiments which have been presented above for the process of the invention for producing an antimicrobial coating composition also apply to the process of the invention for coating an implant with an antibacterial coating.

To clean the coating, the binding of the coating composition can be followed by a washing step and a drying step.

Furthermore, the implant can undergo customary preparation steps, e.g. polishing of the surface in order to obtain a desired surface roughness, for example a surface roughness of 0.013 μm or less, before coating.

An advantageous further development of the process provides for the application of the solution of the coating composition to be carried out by spin coating (in particular in the case of planar substrates) or a dipping or spraying process. This simplifies the process procedure and gives a coating having a particularly uniform layer thickness.

A very good reactivity of the coating composition with the implant surface to form an even layer thickness is advantageously obtained by a concentration of the coating composition in the solvent being from 2 to 20 mg/ml and in particular from 8 to 12 mg/ml.

Furthermore, the invention also describes an antimicrobially coated implant. The antimicrobially coated implant is produced by the above-described process for coating an implant with an antibacterial coating. The implant of the invention is made of titanium, zirconium, tantalum, stainless steel or zirconium oxide and has an average layer thickness of the antimicrobial coating of from 5 to 50 nm and in particular from 15 to 25 nm. The layer thickness is determined by ellipsometry. The layer thickness obtained in the implant of the invention by means of the process of the invention is about 10 nm higher than those obtained by alternative processes for producing a coating composition under otherwise identical conditions. This indicates that the chemical structure of the coating composition is not the same as the structures of the coating compositions produced in a different sequence. Examples of implants according to the invention encompass dental implants, implants for hip and knee endoprostheses and also heart pacemakers. Particularly in tumour therapy, when immunosuppressed patients are given large implants, infection prophylaxis is of tremendous importance. The present invention is particularly useful for, in particular, dental implants which are by their nature in contact with the oral cavity which has a high population of bacteria and are therefore subjected to a particular infection risk.

Figure 2:
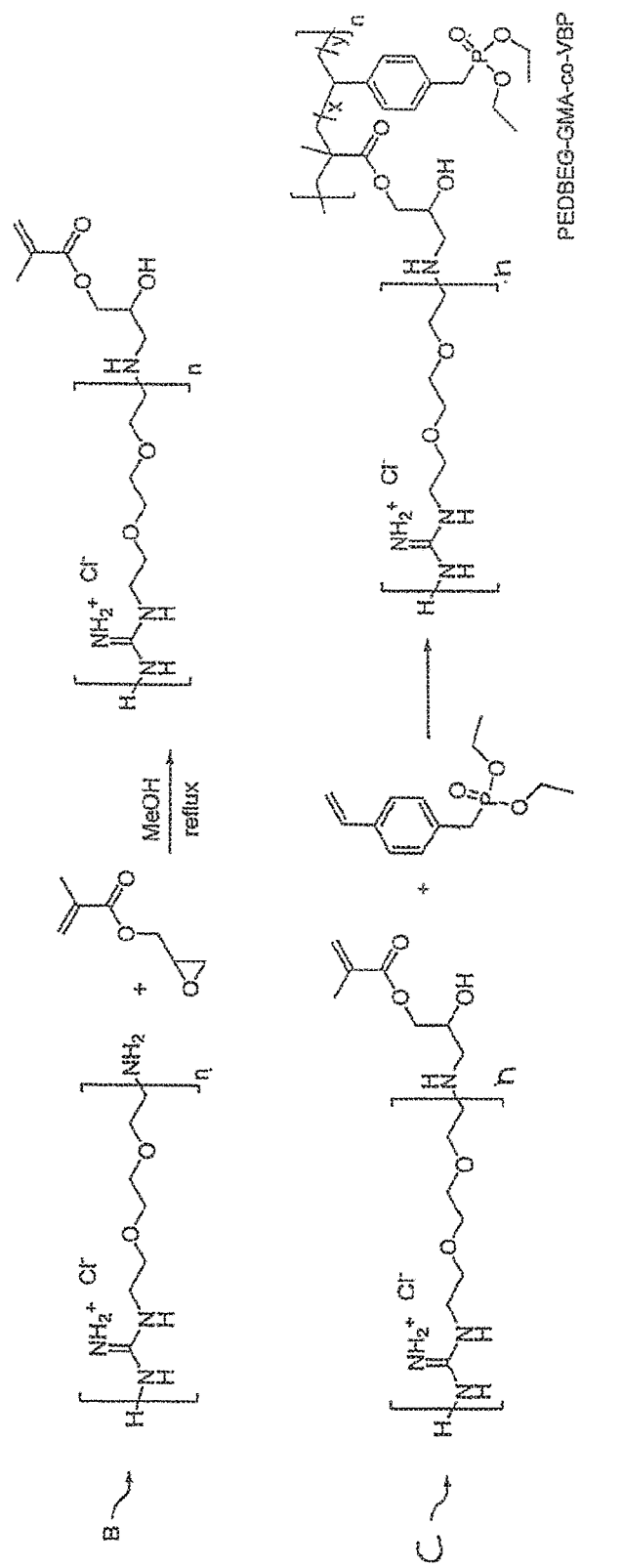
Figure 3:
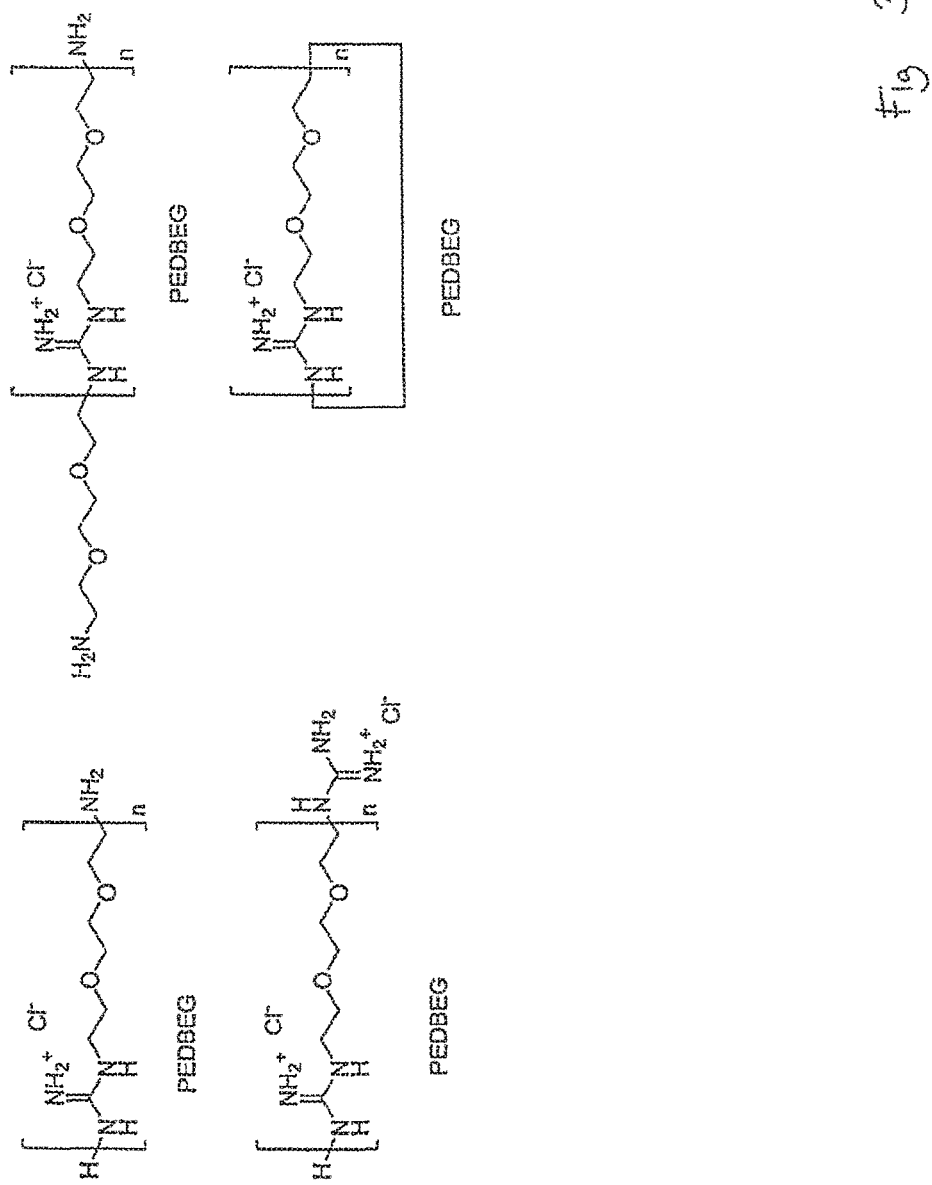
Figure 4:
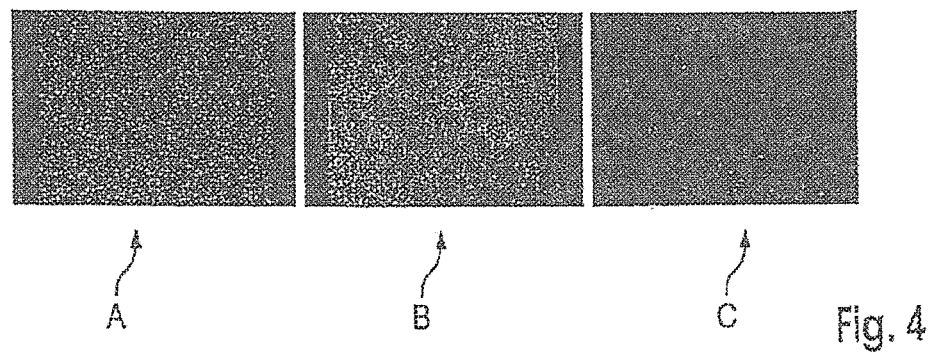
Figure 5:
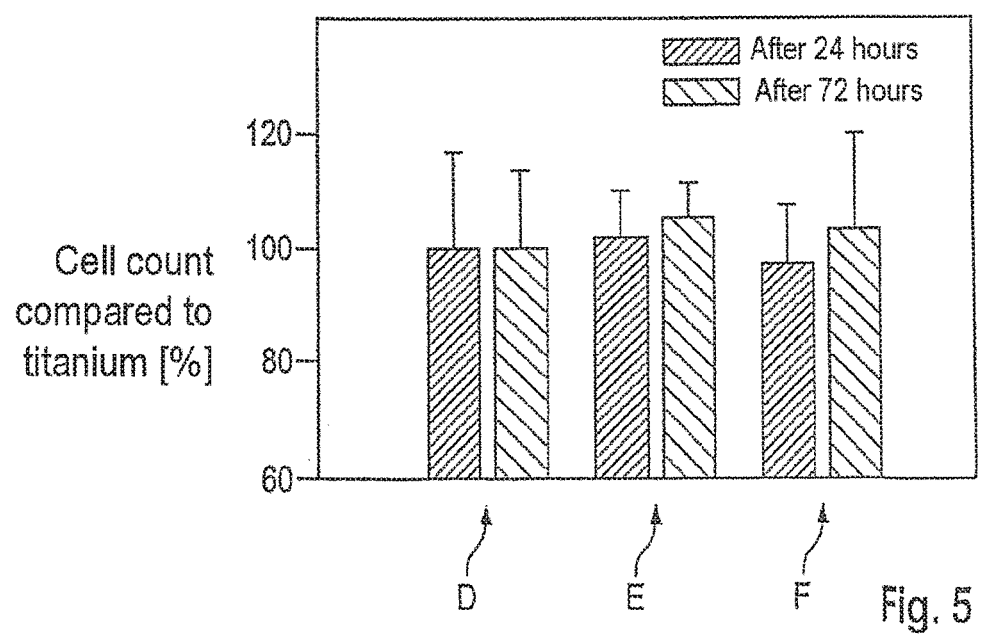

Further details, advantages and features of the present invention can be derived from the following description of working examples with the aid of the drawing. The drawing shows:

FIG. 1 a reaction scheme for producing an antimicrobial coating composition according to a first embodiment of the invention, FIG. 2 a reaction scheme for producing an antimicrobial coating composition according to a second embodiment of the invention, FIG. 3 an overview of possible structures of PEDBEG, FIG. 4 a schematic depiction of micrographs after colonization by *Staphylococcus aureus*, and FIG. 5 a graph showing the cell count of adhering gingiva fibroblasts after 24 hours and 72 hours.

The present invention will be explained in detail with the aid of working examples. Here, only the aspects of the invention which are essential to the invention are presented, all other aspects will be left out in the interests of clarity.

In detail, FIG. 1 shows a reaction scheme for producing an antimicrobial coating composition for the example of copolymer PEDBEG-GMA-co-DMMEP. Reaction step A is the synthesis of PEDBEG by polycondensation of guanidine hydrochloride and 2,2-(ethylenedioxy)bis(ethylamine), where n is preferably 5. For this purpose, 50 mmol (7.41 g) of 2,2-(ethylenedioxy)bis(ethylamine) and 525 mmol (5 g) of guanidine hydrochloride are placed in a 50 ml three-neck flask provided with mechanical stirrer. The reaction mixture is heated to 170° C. over a period of 30 minutes and then stirred at this temperature under a nitrogen atmosphere for 300 minutes. The ammonia liberated during the reaction is passed through an aqueous hydrochloric acid solution and thus neutralized. After the reaction, ammonia still present in the reaction mixture is removed by stirring for 40 minutes at 170° C. under reduced pressure. The product is a yellowish viscous solution which becomes solid on cooling.

Reaction step B is the coupling reaction of the PEDBEG oligomers obtained in reaction step A with 2,3-epoxypropyl methacrylate (glycidyl methacrylate—GMA) (monomer A) to give a (meth)acrylic acid-polyguanidine macromolecule. Only one structure of a PEDBEG oligomer is shown by way of example. As regards further structures, reference is made for completeness to FIG. 3. 5 mmol of PEDBEG (5 g) together with 20 ml of methanol are placed in a 50 ml two-neck flask and 150 mg of GMA (1.2 mmol) are then added. The solution is refluxed for 40 hours. It is worked up by taking off the solvent under reduced pressure.

In reaction step C, the copolymerization of PEDBEG-GMA with 2-(dimethoxyphosphoryl)ethyl methacrylate (DMMEP) (monomer B) is carried out as a free-radical copolymerization in methanol using AIBN as free-radical initiator. For this purpose, a one molar solution of the monomer B in methanol is prepared. In addition, an initiator solution containing 164 mg of AIBN in 10 ml of methanol is made up. The batches have a volume of 5 ml and are produced in a 1:1 ratio of phosphonate to PEDBEG-GMA with 0.5 ml of initiator solution in each case. The screw-cap reagent bottles are flushed with nitrogen for two minutes to remove oxygen and then firmly closed. The copolymerization is carried out at 60° C. for 14 hours and stopped by dipping into ice water. The work-up is carried out by precipitation of the polymers in cold diethyl ether, filtration with suction on POR2 frits and drying under reduced pressure for three days at room temperature. In the PEDBEG-GMA-co-DMMEP obtained, x is approximately 23 mol % and y is approximately 67 mol %.

The resulting coating composition, viz. the copolymer PEDBEG-GMA-co-DMMEP, displays a high readiness to bind to conventional implant surfaces such as titanium, stainless steel, zirconium, tantalum and zirconium oxide.

To bind the coating composition to an implant surface, PEDBEG-GMA-co-DMMEP was applied as a solution having a concentration of 10 g/l in methanol to degreased samples of implant surfaces (e.g. titanium grade 5), stored at 120° C. for 16 hours to bind the coating composition and then washed twice with the solvent methanol in an ultrasonic bath for in each case 20 minutes.

The antimicrobial implant produced in this way displayed excellent antimicrobial properties and was very cell-compatible.

FIG. 2 shows the reaction steps B and C of FIG. 1 for a copolymerization of PEDBEG-GMA with diethyl (4-vinylbenzyl)phosphonate (VBP). The chemical reaction is carried out in a manner analogous to the description for FIG. 1.

The coating composition obtained according to FIG. 2, viz. the copolymer PEDBEG-GMA-co-VBP, in which x is approximately 23 mol % and y is approximately 67 mol %, displays a high readiness to bind to conventional implant surfaces such as titanium, stainless steel, zirconium, tantalum and zirconium oxide. To bind the coating composition to an implant surface, PEDBEG-GMA-co-VBP was applied as a solution having a concentration of 10 g/l in methanol to degreased samples of implant surfaces (e.g. titanium grade 5), stored at 120° C. for 16 hours to bind the coating composition and then washed twice with the solvent methanol in an ultrasonic bath for in each case 20 minutes.

FIG. 3 gives an overview of possible oligomeric structures of PEDBEG, where n is preferably 5.

FIG. 4 is a schematic depiction of micrographs after colonization with *Staphylococcus aureus*. For this purpose, bacteria (*Staphylococcus aureus*) were sown on the surface of implant samples A, B and C and cultivated for 24 hours. The adhering bacteria were subsequently stained with a fluorescent dye and made visible. Implant sample A was titanium (grade 5) without antimicrobial coating, implant sample B was titanium (grade 5) coated with VBP-GMA+PEDBEG and implant sample C was coated with coating composition produced according to the reaction scheme in FIG. 1 (PEDBEG-GMA-co-DMMEP 67% mol % of DMMEP).

As regards implant sample B, it may be said that the coating was produced by firstly polymerizing VBP with GMA, binding the copolymer to the titanium and only then carrying out a further reaction with PEDBEG.

In FIG. 4, a reduction in the number of germs on the PEDBEG-GMA-co-DMMEP coating can clearly be seen, while strong germ growth was observed on the coating of implant sample B and on implant sample A.

Furthermore, the cell compatibility of implant samples was examined. The results are shown in the graph in FIG. 5. For this purpose, implant samples D, E and F were produced as follows: implant sample D: titanium (grade 5), implant sample E (comparative example): titanium (grade 5) coated with GMA-co-VBP+PEDBEG and implant sample F (example according to the invention): titanium (grade 5) coated with PEDBEG-GMA-co-DMMEP and colonized with human gingiva fibroblasts (HGFib). Here, both adhesion and proliferation of the cells on the surfaces were assessed. The results for adhesion were examined after 24 hours and the results of proliferation were examined after 72 hours.

As regards implant sample E, it may be said that the coating was produced by firstly polymerizing VBP with GMA, binding the copolymer to the titanium and only then carrying out a further reaction with PEDBEG.

The adhesion of HGFib to the implant sample E is at the same level as in the case of bare titanium (D). A slightly better value is obtained for proliferation. The adhesion of HGFib on the implant sample F is at a level similar to the case of bare titanium (D). Even a slightly better value is obtained for proliferation. The coating composition PEDBEG-GMA-co-DMMEP according to the invention thus does not not have an adverse effect on HGFib cells in the adhesion test. The coating composition according to the invention displayed excellent biocompatibility.

To supplement the disclosure of the above written description of the invention, reference is explicitly made to the pictorial illustration of the invention in FIGS. 1 to 5.

The invention claimed is:

1. A process for producing an antibacterial coating composition for implants, which comprises the steps of:
    reaction of a monomer A which is based on (meth)acrylic acid and contains an epoxide with a polyguanidine by reaction of an amino group of the polyguanidine with the epoxide to give a (meth)acrylic acid-polyguanidine macro-molecule having a (meth)acrylic acid unit; and
    polymerization of the (meth)acrylic acid-polyguanidine macromolecule with a monomer B which contains a polymerizable double bond and at least one phosphonate group by free-radical polymerization of the (meth)acrylic acid unit and the polymerizable double bond;
    wherein the polyguanidine is prepared by reaction of guanidine hydrochloride with 1,2-bis(2-aminoethoxy)ethane and has at least one of the following formulae:

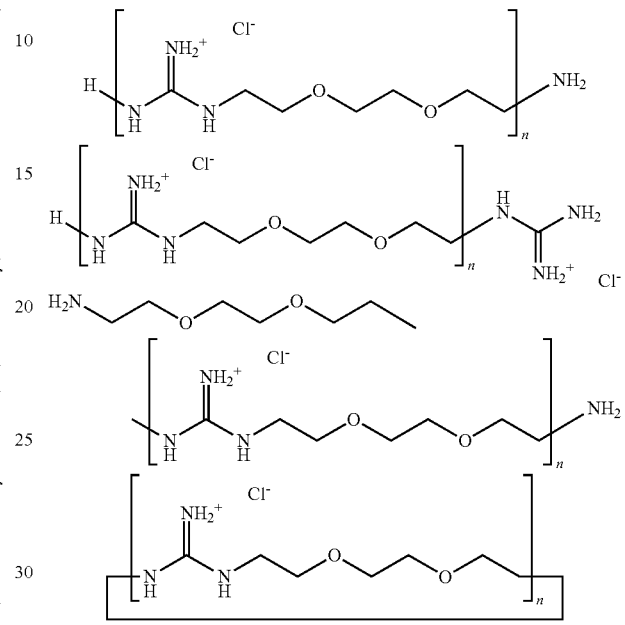

where n is an integer in the range from 2 to 10.

2. The process according to claim 1, wherein the monomer A is 2,3-epoxypropyl methacrylate.

3. The process according to claim 1, wherein the monomer B is diethyl (4-vinylbenzyl)phosphonate, 2-(dimethoxyphosphoryl)ethyl methacrylate or 2-(dimethoxyphosphoryl) methyl methacrylate.

4. The process according to claim 1, wherein the polyguanidine is poly-2-(2-ethoxy)ethoxyethylguanidine hydrochloride.

5. The process according to claim 1, wherein a proportion of the monomer B based on the antibacterial coating composition is about 67 mol %.

6. A process for coating an implant with an antibacterial coating, which comprises the steps of:
    reaction of a monomer A which is based on (meth)acrylic acid and contains an epoxide with a polyguanidine by reaction of an amino group of the polyguanidine with the epoxide to give a (meth)acrylic acid-polyguanidine macromolecule having a (meth)acrylic acid unit,
    polymerization of the (meth)acrylic acid-polyguanidine macromolecule with a monomer B which contains a polymerizable double bond and at least one phosphonate group by free-radical polymerization of thea (meth)acrylic acid unit and the polymerizable double bond to produce a coating composition,
    dissolution of the coating composition in a solvent to form a solution of the coating composition,
    provision and degreasing of an implant,
    application of the solution of the coating composition to the implant and
    binding of the coating composition to the implant under action of temperatures in a range from 50 to 200° C.

7. The process according to claim 6, and further comprising washing and subsequently drying the implant after binding of the coating composition.

8. The process according to claim 6, wherein the application of the solution of the coating composition is performed by spin coating or a dipping process or a spraying process.

9. The process according to claim 6, wherein a concentration of the coating composition in the solvent is from 2 to 20 mg/ml.

10. The process according to claim 6, and further comprising providing that the implant consists of titanium, zirconium, tantalum, stainless steel or zirconium oxide and an average layer thickness of the antibacterial coating is from 5 to 50 nm.

11. The process according to claim 10, and further comprising providing that the average layer thickness of the antibacterial coating is from 15 to 25 nm.

12. The process according to claim 9, wherein the concentration of the coating composition in the solvent is from 8 to 12 mg/ml.

13. The process according to claim 1, where n is an integer in a range from 3 to 6.

14. The process according to claim 13, where n is 5.

* * * * *